United States Patent [19]

Singh et al.

[11] Patent Number: 5,618,515

[45] Date of Patent: Apr. 8, 1997

[54] AEROSOL SPRAY COMPOSITION FOR THE TREATMENT OF DERMAL BURNS BY COOLING AND ANESTHETIZING THE WOUND AND VALVED CONTAINER FOR DISPENSING SAME

[75] Inventors: Mohinder Singh, Naperville, Ill.; Lisa Vail, Bethlehem; Raymond S. Niedbala, Allentown, both of Pa.

[73] Assignee: Blistex Inc., Oak Brook, Ill.

[21] Appl. No.: 170,022

[22] Filed: Feb. 7, 1994

Related U.S. Application Data

[62] Division of Ser. No. 932,898, Aug. 19, 1992, abandoned.

[51] Int. Cl.$^6$ ...................................................... A61K 9/12
[52] U.S. Cl. .............................. 424/45; 424/47; 514/817; 514/887
[58] Field of Search ........................ 128/200.14; 424/45, 424/47, 78.03; 514/817, 887, 873

[56] References Cited

U.S. PATENT DOCUMENTS

| | | | |
|---|---|---|---|
| 3,708,431 | 1/1973 | Prussin | 252/188.3 |
| 4,439,342 | 3/1984 | Albanese | 252/305 |
| 4,814,161 | 3/1989 | Jinks et al. | 424/45 |
| 4,946,870 | 8/1990 | Partain, III et al. | 514/777 |
| 4,976,953 | 12/1990 | Orr et al. | 424/47 |
| 5,045,565 | 9/1991 | Gardner et al. | 514/487 |
| 5,223,244 | 6/1993 | Moro et al. | 424/45 |
| 5,225,183 | 7/1993 | Purewal et al. | 424/45 |
| 5,284,133 | 2/1994 | Burns et al. | 128/200.14 |

OTHER PUBLICATIONS

The Merck Index, 9th Ed., Windholz et al. editors, 1976, pp. 792, 5940.

*Primary Examiner*—Raj Bawa
*Attorney, Agent, or Firm*—Brezina & Ehrlich

[57] ABSTRACT

A composition is provided for the treatment of dermal burns and is composed of a homogeneous solution of skin conditioners, anesthetics, water, and alcohol in combination with dimethyl ether. The use of dimethyl ether as the propellant and solvent forms a homogeneous solution of ingredients which otherwise have little solubility in each other. This formulation also cools the skin when applied, significantly improving the healing of the burns. A pressurized aerosol container is also provided having a metered dose valve for accurately dispensing metered doses of the dermal burn composition to optimize treatment and prevent freezing of the skin.

1 Claim, 1 Drawing Sheet

AEROSOL SPRAY COMPOSITION FOR THE TREATMENT OF DERMAL BURNS BY COOLING AND ANESTHETIZING THE WOUND AND VALVED CONTAINER FOR DISPENSING SAME

This is a division of application Ser. No. 07/932,898, filed Aug. 19, 1992, now abandoned.

BACKGROUND OF THE INVENTION

The present invention relates generally to compositions used to treat dermal burns, and specifically to such compositions formulated for use as aerosol sprays, and to a valved container for dispensing a metered amount of the composition.

Dermal burns are common in our homes and work places. However, the current non-prescription treatment for such burns is simply to run cold water over the burn, and/or cover the burn and treat it with antibiotics. Research has shown that the extent of injury from a burn can be minimized if the burn is cooled within one hour of injury. This also gives the patient pain relief, as is evident when ice or cold water is applied to a fresh burn.

However, this type of cold treatment cannot protect the patient from infection or provide long-term relief of pain. To accomplish this, an antibiotic and an anesthetic should be used. Products containing topical anesthetics and antibiotics are commercially available. They are sold as sprays, gels, ointments, and creams. Conventional spray treatments incorporate alcohol which, upon application, creates a brief cooling sensation upon evaporation. However, none can significantly lower the dermal temperature when applied to a burn.

Accordingly, it is an object of the invention to provide a composition for treating dermal burns which cools the burn upon contact.

It is another object of the invention to provide a sprayable dermal burn treatment which both cools and anesthetizes the burn area.

It is a further object of the invention to provide a sprayable dermal burn treatment which cools, anesthetizes, and conditions the burned skin to promote healing.

It is yet another object of the invention to provide a sprayable dermal burn treatment in a container which meters the dosage to avoid lowering skin temperature below desired limits.

It is still another object of the invention to provide a metered valve for an aerosol container which is suitable for dispensing appropriately metered doses of medications such as dermal burn treatments.

SUMMARY OF THE INVENTION

The above-identified objects are achieved by providing a composition for treating dermal burns, wherein the composition includes a solution of at least one skin conditioner, at least one anesthetic, water and a solvent in combination with dimethyl ether, wherein dimethyl ether serves as an aerosol propellant and also cools the burned skin.

The present invention also contemplates a product for treating dermal burns, including a container having a metered dose valve, a composition for treating dermal burns being stored under pressure in the container, the composition including a solution of at least one skin conditioner, at least one anesthetic, water and a solvent in combination with dimethyl ether, wherein dimethyl ether serves as an aerosol propellant and also cools the burned skin.

In addition, the present invention provides a specialized metered dose vane for dispensing medications such as the present dermal burn treatment, so that specifically metered amounts of medication are dispensed from the aerosol container. The valve includes a valve housing adapted for sealed engagement at an open upper end of the container and having a central hollow portion defining a metering chamber, a valve stem having an upper end provided with an actuator, a hollow portion in fluid communication with the actuator and having a stem orifice, and a lower portion. The valve stem is configured for reciprocal vertical movement in the central hollow portion of the vane housing to alternately open and close the upper and lower ends of the metering chamber, respectively. Also included in the valve is a biasing device for biasing the valve stem in a closed position in which the stem orifice is vented to the atmosphere, and in which the metering chamber receives a dose of the contents of the container when its upper end is closed by the vane stem. Upon the depression of the actuator which overcomes the biasing force, the stem orifice is positioned to be in fluid communication with the metering chamber and permits the evacuation of the contents from the metering chamber through a channel in the actuator.

Furthermore, the invention includes a method for treating burned skin, including providing a product for treating burns including a container having a metered dose valve. The container is filled with a composition for treating dermal burns being stored under pressure in the container, the composition includes a solution of at least one skin conditioner, at least one anesthetic, water and a solvent in combination with dimethyl ether, wherein dimethyl ether serves as an aerosol propellant and also cools the burned skin. The method includes spraying the composition upon a burned area of skin so that approximately 0.01 ml to 15 ml of the composition is sprayed upon the burned area of skin per spray dose.

DESCRIPTION OF THE PREFERRED EMBODIMENT

Figure 1:
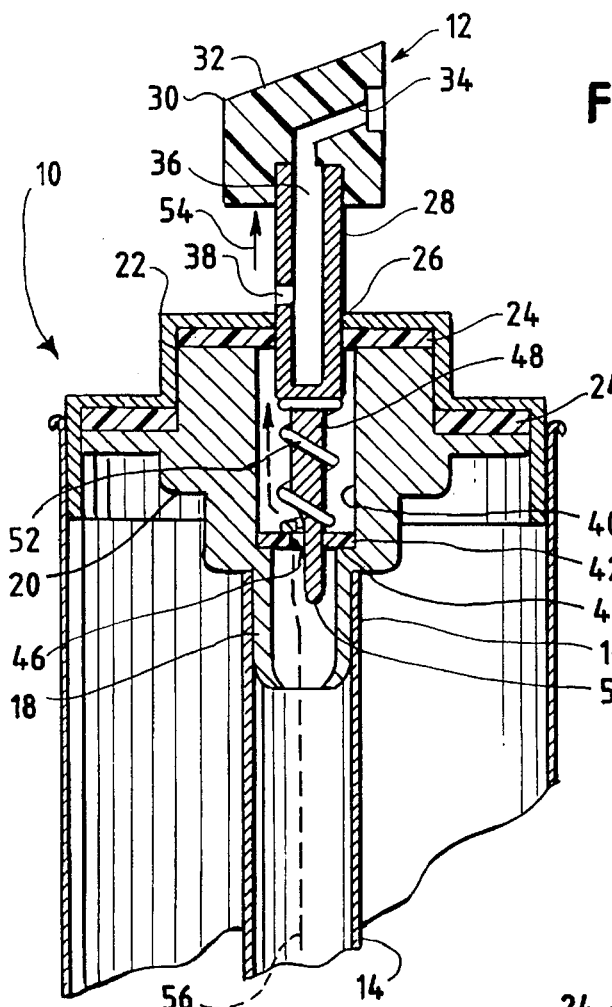
FIG. 1 is a vertical sectional view of an aerosol container of the type suitable for use with the present composition, wherein the container is illustrated with the present metering valve in the fill or closed position.

The present invention presents various compositions which cool the dermis upon application. In addition, these compositions may include topical anesthetics, antibiotics, skin conditioners, and solvents which are delivered with the application of the composition. The compositions of the invention are preferably delivered from a pressurized container utilizing a valve that allows precise dosing to the affected areas.

In the preferred embodiment, in order to accomplish cooling of the dermis, dimethyl ether is used as an aerosol propellant. This liquified gas is available commercially and is finding widespread use in aerosols since it does not appear to harm the ozone layer. Although other ethers may be suitable for cooling the skin, dimethyl ether is preferred in the present invention for safety reasons.

Dimethyl ether, the preferred ether in the present composition, has already been used in several products for various applications. U.S. Pat. No. 4,482,662 discloses the use of dimethyl ether for solubilizing aerosol paint components. U.S. Pat. Nos. 4,466,838 and 4,450,253 disclose the use of dimethyl ether in a propellant system. Further, U.S. Pat. No. 4,990,192 discloses the use of dimethyl ether for delivery of adhesives useful for the removal of lint. Finally, U.S. Pat. No. 4,716,032 discloses the use of dimethyl ether in a treatment for bovine mastitis.

Such varied uses demonstrate the utility of dimethyl ether. The wide applicability of dimethyl ether is due largely to its abilities as a solvent. It can solubilize many combinations of materials which are normally immiscible. This characteristic is an important feature of the present invention.

The present invention is composed of several materials. These include, but are not limited to, active ingredients, skin protectants, film formers, solvents, and propellant. Finally, the composition is placed in a sealed container utilizing a metered dose valve to deliver the composition.

Active ingredients may include anesthetics, antibiotics, and anti-inflammatory drugs. Examples of these drugs include the anesthetics benzocaine, lidocaine, tetracaine, and dibucaine; the antibiotics polymyxin B and bacitracin; and the anti-inflammatory hydrocortisone. A broad range of use is 0.01 percent to 25 percent of the composition. The preferred range for antibiotics is between 0.01 percent and 5 percent, and for the anti-inflammatory drugs is between 0.01 percent and 4 percent.

Skin conditioners such as protectants and film formers have similar functions in that they provide a barrier to outside agents once applied to the burn site. Some examples of these materials include polyvinyl pyrrolidone, polysorbate 20, silicones, gums such as carrageenan, and inorganic materials such as titanium dioxide. These materials may be used in a broad range from 0.5 to 10 percent of the composition, with a preferred range of 1.0 to 4.0 percent.

Solvents act as carriers for the other ingredients, although they can add to the aesthetic feel of the composition. Typical solvents include polyhydric alcohols, ethanol, propylene glycol, water, mineral oil, and silicone. These materials may be used in a broad range of 1.0 to 50 percent, with a preferred range of 5 to 20 percent.

Finally, each composition contains a propellant. The preferred propellant in the invention is dimethyl ether. However, the dimethyl ether may be combined with other propellants such as a butane, propane, freon, carbon dioxide, or nitrogen. The propellant may compose 25 to 95 percent of the composition. The preferred range is 50 to 80 percent.

In some instances, compositions of the constituents of the above-identified classes of ingredients are normally immiscible and must be provided with an agent for allowing solubilization. An example is a homogeneous solution of benzocaine and water in the presence of dimethyl ether. The dimethyl ether couples the benzocaine and water into a stable homogeneous solution.

Referring now to FIG. 1, the container for the compositions, generally designated 10, may be composed of various materials including tin, steel, aluminum, or other alloys. The key is that the container 10 withstand the pressure of the propellant mixture. The amount of pressure exerted by the propellant will vary depending upon the mixture used. As an example, the pressure of dimethyl ether at 130 degrees centigrade is 180 psia. This is the common pressure for aerosol cans and is acceptable to the United States Department of Transportation as per the Code of Federal Regulations, Section 178.4.

To deliver the compositions accurately, a metered dose valve 12 is sealingly disposed in an open upper end of the container as is known in the art. A metered dose valve is necessary for the proposed invention since dimethyl ether, if applied freely, could freeze the dermis to minus 35 to minus 40 degrees centigrade. Thus, care must be taken to avoid applying excess solution to the burned area. It has been found that the valve 12 consistently provides the desired dosage.

A dip tube 14 extends into the aerosol container 10, and has an upper part 16 which attaches to a flange 18 of a valve housing 20. A cap 22 sits over the vane housing 20 and is separated from the valve housing 20 by means of gaskets 24. An aperture 26 is centrally located and extends through the upper portion of cap 22. A valve stem 28 extends through the aperture 26 and into the upper portion of valve housing 20. Sitting atop the valve stem 28 is an actuator 30 having a slanted upper portion 32 for actuation by a thumb or other means. The actuator 30 has a channel 34 leading from the exterior to a central portion of the actuator, which channel is connected to a hollow portion 36 in valve stem 28. A stem orifice 38 connects the hollow portion 36 of the vane stem 28 to the atmosphere in the closed or fill position shown in FIG. 1.

Valve stem 28 is adapted for reciprocal vertical movement through aperture 26 and into a metering chamber 40 which is formed in the central hollow portion of valve housing 20. The lower portion of metering chamber 40 is defined by a gasket 42 which rests on a flange 44. Gasket 42 has an aperture 46 of predetermined diameter extending therethrough. Valve stem 28 has a central portion 48 of a lesser diameter than the upper portion of valve stem 28, and a third lower portion 50 of a lesser diameter than portion 48. Portion 50 extends through aperture 46 in gasket 42. The diameter of lower portion 50 of valve stem 28 is considerably less than the diameter of aperture 46 through gasket 42, while the diameter of portion 48 of valve stem 28 is approximately the same size as the diameter of aperture 46. Lower portion 50 acts as a guide to stabilize the vertical movement of vane stem 28.

The purpose of the metering valve 12 is to ensure that only a small, predetermined amount of the contents of the aerosol container 10 can be ejected from the container each time the actuator 30 is depressed. A spring 52 extends between gasket 42 and a lower flanged portion of valve stem 28 to exert a biasing force which urges the valve stem 28 upward as shown by the arrow 54 in FIG. 1. FIG. 1 illustrates the metering valve 12 in its unactuated fill or closed position, wherein the hollow chamber 36 of the valve stem 28 and the channel 34 are evacuated to the atmosphere through stem orifice 38. In this position, the chemical composition which is pressurized in the aerosol container 10 migrates up the dip tube 14 through an open bottom (not shown), and is forced through a portion of aperture 46 into the metering chamber 40 as shown by the dashed arrow 56.

When the spring 52 raises the actuator 30 and valve stem 28 to its uppermost position as shown in FIG. 1, the middle portion 48 of the valve stem 28 extends above and does not block aperture 46 through gasket 42. Since the diameter of lower portion 50 of valve stem 28 is considerably less than aperture 46, aperture 46 is not blocked, and the chemical composition in the aerosol container 10 flows freely through the dip tube 14 and into metering chamber 40. However, because the outer diameter of valve stem 28 at its upper portion is the same as, and tightly held through, the aperture 26 in cap portion 22, none of the compressed chemical contents of metering chamber 40 can flow into the hollow portion 36 and the channel 34 of vane stem 28 and actuator 30, respectively.

Figure 2:
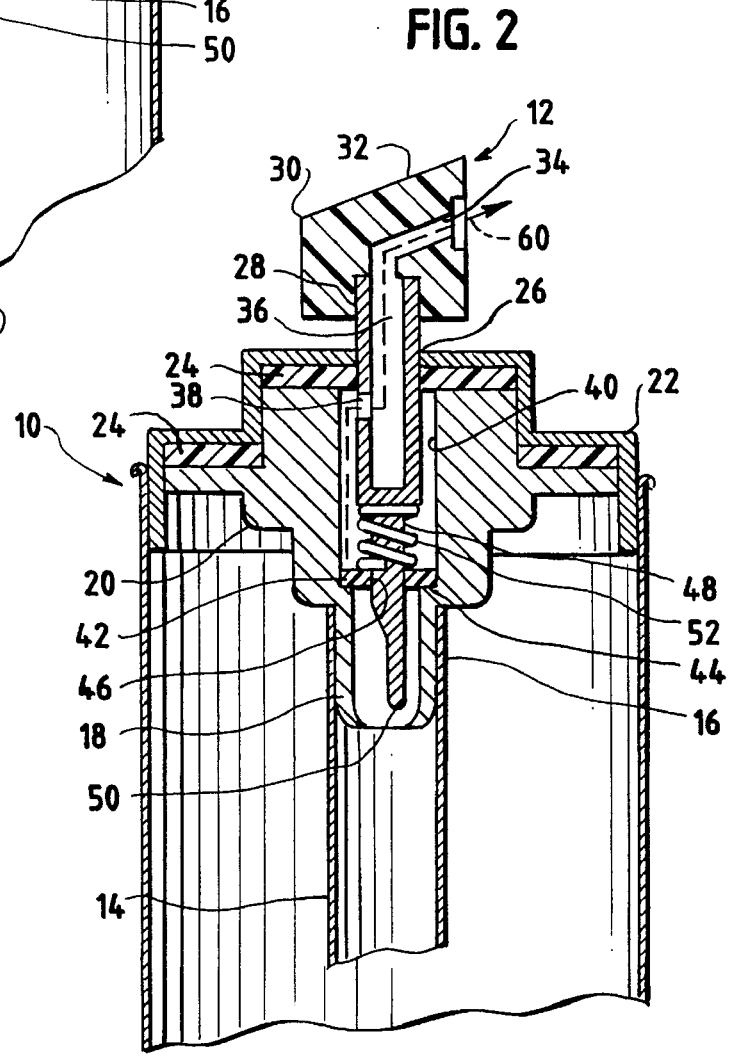
FIG. 2 is a vertical sectional view of the container of FIG. 1, with the valve shown in the discharge or open position.

Upon actuation of the metering valve 12, thumb or other actuating pressure is applied downward to slanted portion 32 of actuator 30 in opposition to the force supplied by spring 52. The spring 52 is thereby compressed, whereby the vane stem 28, actuator 30, and spring assume the discharge or open position shown in FIG. 2. In the position shown in FIG. 2, the middle portion 48 of vane stem 28 extends into aperture 46 in gasket 42, and since the diameter of middle portion 48 is approximately the same as the diameter of aperture 46, the middle portion 48 of valve stem 28 effectively blocks fluid communication between the dip tube 14 and metering chamber 40. However, stem orifice 38 in the position shown in FIG. 2 is positioned in the metering chamber 40, and provides a passageway designated by the dashed line 60 for the pressured fluid in the metering chamber through stem orifice 38, into hollow portion 36 of valve stem 28, and out of channel 34 in actuator 30. This allows the pressurized chemical composition in the metering chamber to be expelled from the metering vane 12 and onto the skin where it is properly applied.

Since no additional chemical composition from dip tube 14 or the aerosol container 10 can enter the metering chamber 40 while the metering vane 12 is in the discharge or open position shown in FIG. 2, each time the actuator 30 is depressed against the force of spring 52, only the amount of chemical composition in metering chamber 40 from the previous position shown in FIG. 1 can be discharged through channel 34. This construction effectively prevents excessive amounts of the chemical composition in the aerosol container 10 from being improperly discharged from the container.

Upon release of thumb or other pressure from actuator 30, the actuator and valve stem 28 assume the position shown in FIG. 1. Chemical composition from the aerosol container 10 again enters the metering chamber, but is also effectively prevented from entering the hollow portion 36 of the valve stem 28 because stem orifice 38 is now outside of the metering chamber. In addition, the engagement of the upper portion of the valve stem 28 in the aperture 26, and with the gasket 24 effectively blocks the escape of any of the chemical composition from the metering chamber 40. Depressing actuator 30 as mentioned above will repeat the process of discharging the chemical composition from the aerosol container through dip tube 14. The metering valve 12 may deliver between 0.01 and 15 ml of the composition, that same amount being retained in the metering chamber 40.

A preferred embodiment of these compositions is shown in the following examples:

EXAMPLES

In each preparation, all materials are mixed prior to placing them in the aerosol container 10 and addition of the dimethyl ether. Typically, the solids are added to the solvent and dissolved or dispersed. The additional ingredients such as film formers, silicones, or skin protectants are then added and stirred.

The materials may then be added to the aerosol container 10. The valve 12 is placed and sealed, and the propellants are added. Typical laboratory equipment used is available from the Laboratory Aerosol Equipment Company, Walton, N.Y.

Some typical compositions are as follows:

| INGREDIENT | #1 % W/W | #2 % W/W | #3 % W/W |
|---|---|---|---|
| PHASE A | | | |
| Benzocaine | 5.0 | 10.0 | 20.0 |
| Polysorbate | 1.0 | 2.0 | 3.0 |
| Polymyxin B | 0.05* | 0.05* | 0.05* |
| Bacitracin | 0.05** | 0.05** | 0.05 |
| Ethanol | 20.0 | 20.0 | 20.0 |
| PHASE B | | | |
| Dimethyl Ether | 73.9 | 65.0 | 55.0 |
| Butane | 0.0 | 2.9 | 1.9 |

*Depends upon International unit ranges between 360 to 650 international units. The range shown on the chart is recorded in the Federal Monograph.
**Depends upon International unit ranges between 4,500 to 13,000 International units. The range shown on the chart is recorded in the Federal Monograph.

The above examples result in clear, homogeneous solutions upon charging of the aerosol container with dimethyl ether.

Furthermore, these compositions when sprayed upon the dermis can temporarily lower the dermal temperature. This provides the immediate pain relief to the burn area followed by long-term pain relief from the anesthetic. Using the preferred embodiment, each spray from the container 10 can deliver sufficient composition to lower the dermal temperature five degrees centigrade.

While a particular embodiment of the aerosol spray composition for the treatment of burns and valved container for dispensing same of the invention has been shown and described, it will be appreciated by those skilled in the art that changes and modifications may be made thereto without departing from the invention in its broader aspects and as set forth in the following claims.

What is claimed is:
1. A composition for treating dermal wounds in a container having a metered dose valve for delivering 0.01 ml to 15 ml of said product per application, said composition consists of: (i) 0.01% to 25% active ingredients by total weight, where the active ingredients are a solution of polysorbate 20 as the skin conditioner in the range of 0.5%–10% by total weight in combination with benzocaine as a topical anesthetic in the range of 0.01%–25% by total weight; (ii) water or ethanol as the solvent in the range of 1.0%–50% by total weight; and (iii) dimethyl ether as the propellant in the range of 25%–95% by total weight.

* * * * *